United States Patent [19]
Zimmon

[11] Patent Number: 5,785,684
[45] Date of Patent: Jul. 28, 1998

[54] APPARATUS AND METHOD FOR THE DEPLOYMENT OF AN ESOPHAGASTRIC BALLOON TAMPONADE DEVICE

[75] Inventor: David S. Zimmon, Port Washington, N.Y.

[73] Assignee: Zimmon Science Corporation, Port Washington, N.Y.

[21] Appl. No.: 597,224

[22] Filed: Feb. 6, 1996

[51] Int. Cl.$^6$ .................................................. A61M 29/00
[52] U.S. Cl. ..................................... 604/96; 606/192
[58] Field of Search ........................... 604/96, 97, 98, 604/99, 101, 11, 15; 606/192–195

[56] References Cited

U.S. PATENT DOCUMENTS

| | | | |
|---|---|---|---|
| 2,687,131 | 8/1954 | Raiche | 606/192 |
| 2,936,760 | 5/1960 | Gants | 606/192 |
| 3,045,677 | 7/1962 | Wallace . | |
| 4,089,337 | 5/1978 | Kronner | 604/96 |
| 4,449,972 | 5/1984 | Kruger . | |
| 4,485,805 | 12/1984 | Foster, Jr. | 604/96 |
| 4,666,433 | 5/1987 | Parks | 604/178 |
| 5,000,743 | 3/1991 | Patel | 604/96 |
| 5,067,497 | 11/1991 | Greear et al. | 604/96 |
| 5,197,948 | 3/1993 | Ghodsian | 604/96 |
| 5,308,326 | 5/1994 | Zimmon . | |
| 5,400,770 | 3/1995 | Nakao et al. . | |
| 5,462,528 | 10/1995 | Roewer . | |
| 5,462,529 | 10/1995 | Simpson et al. . | |

*Primary Examiner*—John G. Weiss
*Assistant Examiner*—David J. Cho
*Attorney, Agent, or Firm*—Woodard, Emhardt, Naughton, Moriarty & McNett

[57] ABSTRACT

A method and apparatus for the deployment of an esophagastric balloon tamponade device within a patient. In one form of the present invention an irrigation tube is positioned through the patient's mouth, esophagus and into the stomach. An inflatable balloon tamponade device is initially positioned around the external surface of the irrigation tube for delivery within the patient. A pushing member is utilized to move the balloon tamponade device along the outer surface of irrigation tube and into a location adjacent internal bleeding sites. An internal obturator passes through an aperture within the irrigation tube to minimize and/or prevent kinking of the tube during passage of the tube into the patient. A plurality of length indicators are formed on the external surface of the tube in order to apprise the practitioner of the depth of insertion of the tube. The present invention provides for the deployment of a balloon tamponade device adbsent a endoscope.

14 Claims, 6 Drawing Sheets

APPARATUS AND METHOD FOR THE DEPLOYMENT OF AN ESOPHAGASTRIC BALLOON TAMPONADE DEVICE

BACKGROUND OF THE INVENTION

The present invention relates generally to the therapeutic treatment of the gastrointestinal tract in a patient having gastrointestinal bleeding. More particularly, one embodiment of the present invention relates to a flexible irrigation tube for deploying a balloon tamponade device in the gastrointestinal tract. While the present invention was developed for use in treating bleeding sites within the gastrointestinal tract, it may have uses in other areas of medicine.

Often it is necessary to treat bleeding sites within the distal esophagus and proximal stomach particularly to control bleeding from esophagastric varices. It is traditional and useful to aspirate the stomach of a patient with gastrointestinal bleeding prior to the practitioner performing any diagnostic or therapeutic procedures. Normally, aspiration of the patient's stomach is performed by passing an oral or nasal gastric tube into the stomach, aspirating the contents which are then examined by the practitioner for the presence of blood, and if blood is present the stomach is irrigated and emptied in preparation for a diagnostic or a therapeutic endoscopic procedure.

Endoscopic examinations require the use of expensive sophisticated equipment under the direction of a physician trained in endoscopy. Therefore, utilizing current therapeutic techniques necessitates that prior to performing an endoscopic examination the the oral and/or nasal tube must be removed and the endoscope passed into the stomach. Subsequently, or as part of the examination the practitioner may attempt to control the bleeding by one of the many therapeutic techniques that are available including: injection of the bleeding site; thermal methods that coagulate the bleeding site; banding, which is the placement of rubber bands around the bleeding site to produce clot formation and stop the bleeding; or the use of a balloon tamponade device. Currently, the deployment of a tamponade balloon to stop variceal bleeding involves backloading the tamponade balloon on the endoscope prior to passage of the tamponade balloon into the patient over the endoscope.

A limitation common to prior therapeutic techniques utilizing endoscopic treatment is the necessity of having a practitioner trained in endoscopy available. Presently, absent the services of a practitioner trained in endoscopy the deployment of the balloon tamponade device is not a treatment alternative. Therefore, there are life threatening situations where the patient can not receive treatment with the balloon tamponade device to control bleeding from the esophageal varices for lack of either a medical facility and/or a trained practitioner. Therefore, the absence of the therapeutic technique and/or the passage of time may compound and complicate the patient's medical condition.

Another limitation associated with the prior therapeutic techniques is the inability to perform irrigation and aspiration while the balloon tamponade device is being deployed. Therefore, the prior techniques require that the stomach be irrigated and the balloon tamponade device be deployed in separate procedures.

A further limitation associated with the prior therapeutic techniques of passing the tamponade device over the endoscope relates to the complex structure of the endoscope, such as a complicated operating handle, an umbilical connection to a light source, and to a suction apparatus. The physical constructs of the endoscope often render the apparatus cumbersome, and requires specialized staff, such as an anesthesiologist, and equipment for tamponade balloon passage not readily available outside of a sophisticated medical treatment facility Although the prior techniques are steps in the right direction for the treatment of esophagastric variceal bleeding, the need for improvement still remains. The present invention satisfies this need in a novel and unobvious way.

SUMMARY OF THE INVENTION

One form of the present invention contemplates an apparatus for controlling esophagastric bleeding within a patient. The apparatus, comprising: an elongated flexible member, a portion of the elongated member passable in the oral-gastric tract of the patient; a tamponade balloon disposed on and slidable along an outer surface of the elongated flexible member; and a pushing member disposed adjacent the tamponade device for moving the tamponade along the flexible member.

Another form of the present invention contemplates a combination for controlling bleeding within a patient. The combination comprising: a flexible tube passable through a patient's mouth and into their stomach; a tamponade balloon for controlling bleeding within the patient's esophagastric area, the tamponade balloon disposed on and slidable along an outer surface of the tube, further the tube having an internal passageway extending therethrough; and obturator extending within the passageway to prevent kinking of the tube during the passage of the tube into the patient.

Another form of the present invention contemplates a method for deploying a tamponade balloon through a patient's mouth and into their stomach for controlling esophagastric bleeding, comprising: providing a flexible tube having a proximal end and a distal end; passing at least a portion of the tube through the patient's mouth and into the stomach, the proximal end of the tube being positionable within the stomach and the distal end of the tube adjacent the mouth; positioning the balloon tamponade around the distal end of the tube adjacent the mouth; and advancing the balloon tamponade along the tube towards the proximal end thereof.

One object of the present invention is to provide an improved apparatus for controlling esophagastric bleeding within a patient.

Another object of the present invention is to provide an improved method for deploying a tamponade balloon within a patient.

Related objects and advantages of the present invention will be apparent from the following description.

DESCRIPTION OF THE PREFERRED EMBODIMENT

Figure 1:
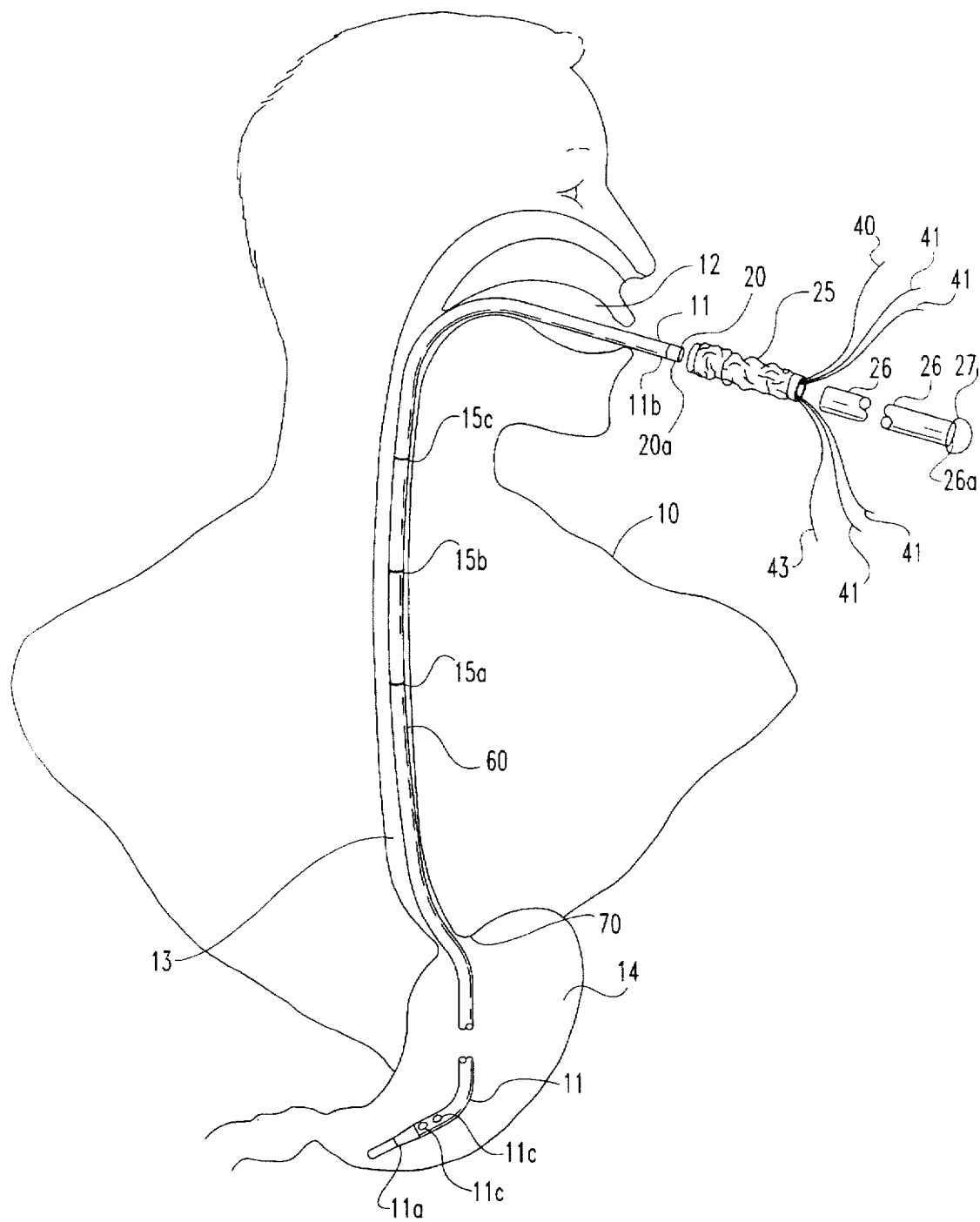
FIG. 1 is a perspective view of a deflated esophagastric balloon tamponade device and irrigation tube according to one form of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring to FIG. 1 there is shown a perspective view of a portion of the gastrointestinal tract of a patient 10. A substantially flexible irrigation tube 11 is placed through the patient's mouth 12, an esophagus 13, and into a stomach 14 to allow irrigation and aspiration of the patient's stomach. Irrigation tube 11 is of sufficient length such that the contents of the stomach can be irrigated/aspirated by the passage of fluid through the tube 11. In the preferred embodiment the irrigation tube 11 has a length of about 120 centimeters (47.25 inches). The irrigation tube 11 is formed of a material that is compatible with human tissue; and in the preferred embodiment is formed of polyvinyl chloride (PVC). The preferred embodiment of irrigation tube 11 has an outside diameter of about 32 fr (10.7 mm). It is understood that other lengths and diameters are within the contemplation of the present invention provided that they provide the desired characteristics.

Irrigation tube 11 includes a proximal end 11a, that is positionable within stomach 14, and a distal end 11b, disposed at the opposite other end of the tube. In the preferred embodiment the proximal end 11a of irrigation tube 11 includes a plurality of apertures therein for receiving gastric contents of the patient therethrough. In one form of the present invention a pair of spaced apertures 11c are formed along the last 10 centimeters of the tube 11. It is understood that other quantities of apertures on the proximal end are within the contemplation of those skilled in the art. A plurality of insertion length indicators are positioned on the exterior surface 60 of the irrigation tube 11. In one form of the present invention the indicators 15a, 15b, and 15c are positioned respectively about 50 centimeters (19.7 inches) from the proximal end 11a, 60 centimeters (23.6 inches) from the proximal end 11a, and 70 centimeters (27.5 inches) from the proximal end 11a of irrigation tube 11. The insertion length indicators 15a, 15b, and 15c assist the practitioner in determining the depth irrigation tube 11 has been introduced within the patient. In the preferred embodiment, the irrigation tube 11 is inserted 60 centimeters (23.6 inches) into the patient thereby leaving approximately 60 centimeters (23.6 inches) of the tube 11 extending outwardly adjacent the patient's mouth 12.

Referring to FIGS. 1-5, there is illustrated the irrigation tube 11 having an internal obturator 20 disposed therethrough. Obturator 20 being slideable and removable from within the irrigation tube 11. In the preferred embodiment obturator 20 passes through an aperture 21 extending the length of the irrigation tube 11. Obturator 20 is designed and constructed to minimize and/or prevent kinking of the irrigation tube 11 as it is passed through the oral cavity, the esophagus 13 and into the stomach 14. Preferably upon completion of the passing of irrigation tube 11 within the gastrointestinal tract the obturator 20 is withdrawn. Withdrawal of the obturator 20 is accomplished by grasping end 20a and slowly moving the obturator 20 outwardly relative to tube 11. Upon the removal of obturator 20 there is a fluid communication pathway defined by aperture 21 extending through irrigation tube 11.

The passage of fluids into and out of the stomach 14 is accomplished through aperture 21. Prudent medical practice often necessitates that the contents of the patient's stomach be aspirated to obtain a sample of the gastric fluid in order to examine for the presence of blood. Further, a wire guide 22 passes through the obturator 20 to facilitate passing the irrigation tube 11 under fluroscopic control. The use of fluroscopic techniques to pass a tube are generally known to those skilled in the art. It is understood by those skilled in the art that the obturator 20 can be tubular, solid, and with or without a wire guide. Variations of the obturator 20 from the preferred embodiment are within the contemplation of the present invention so long as they provide the essential characteristics needed therein.

A balloon tamponade device 25 is designed and manufactured for deployment over the irrigation tube 11 in order to facilitate delivery within the patient. In FIG. 1 the balloon tamponade device 25 is shown in a uninflated condition, that is normally used to introduce the balloon within the patient. A pushing member 26 is utilized to advance the uninflated balloon tamponade device 25 along the outer surface of the irrigation tube 11 and into the stomach 14. In the preferred embodiment the pushing member 26 is a substantially cylindrical tube having a length of about 40 centimeters (15.95 inches) and is formed of polyvinyl chloride. It is understood that pushing member 26 can have other geometric shapes and be formed from a variety of materials. Disposed on an end 26a of the pushing member 26 is a pushing tube controller 27. In the preferred embodiment the pushing tube controller 27 defines a loop or ring designed for grasping by the practitioner.

Figure 1A:
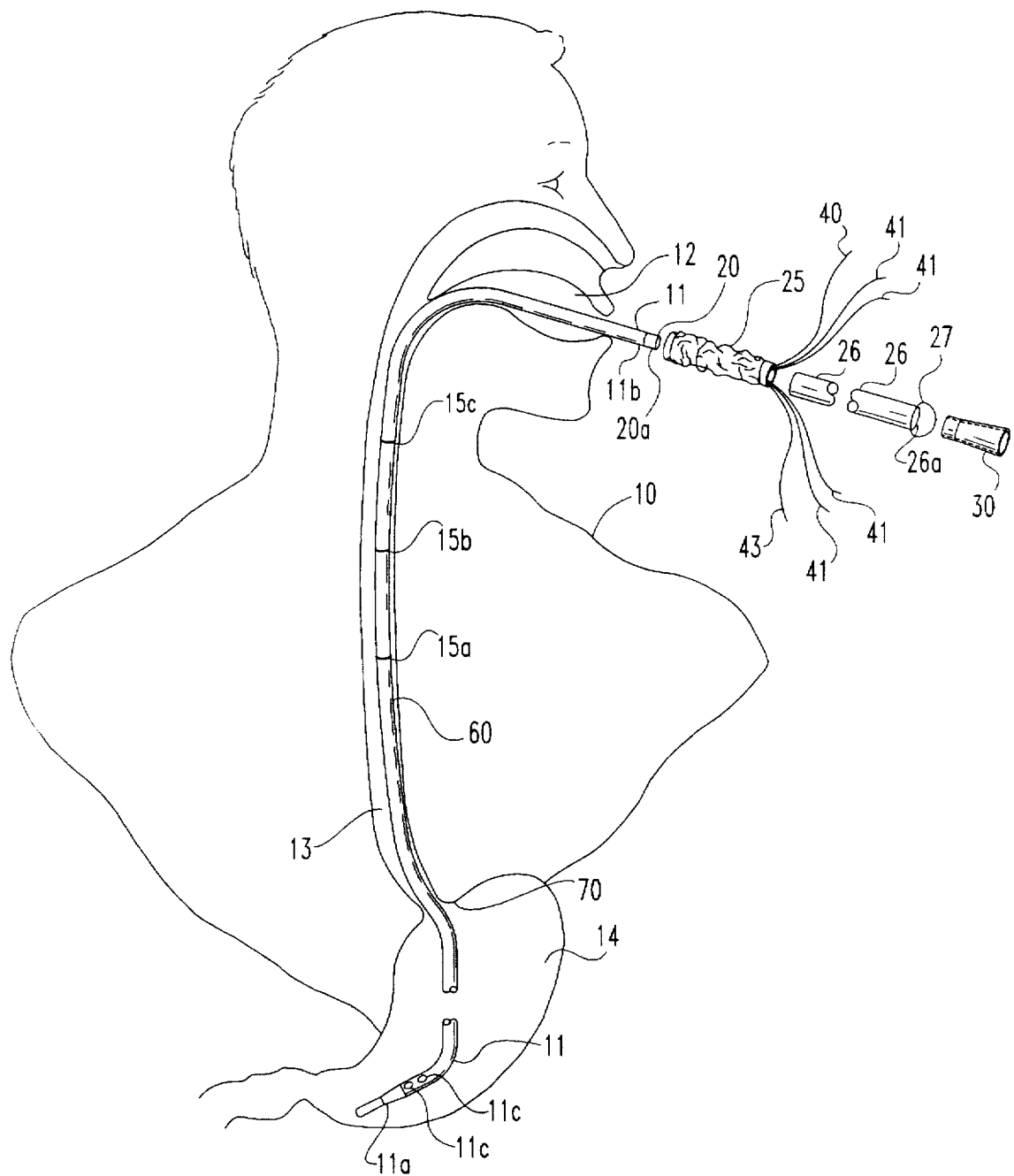
FIG. 1a is a perspective view of a deflated esophagastric balloon tamponade device and irrigation tube according to another form of the present invention.

Referring to FIG. 1a, there is illustrated another form of the present invention. The apparatus illustrated in FIG. 1a is substantially identical to the apparatus set forth in FIG. 1 with the exception that a fluid connecting adaptor 30 has been introduced in FIG. 1a. Fluid connecting adaptor 30 is removable from the irrigation tube 11 and allows for the balloon tamponade device 25 to be loaded on the tube and, then the irrigation tube 11 is connected to the adapter 30 and the other end of adapter 30 is connected to an external fluid or suction source. This adapter facilitates the introduction of fluid or suction to the irrigation tube 11 by an external suction or fluid device. More particularly, fluid connecting adaptor 30 is of a conical shape to allow the coupling of two separate tubes. Further, individuals having ordinary skill in the art will appreciate that there are other types of adapters available to connect two tubes in fluid communication.

Figure 2:
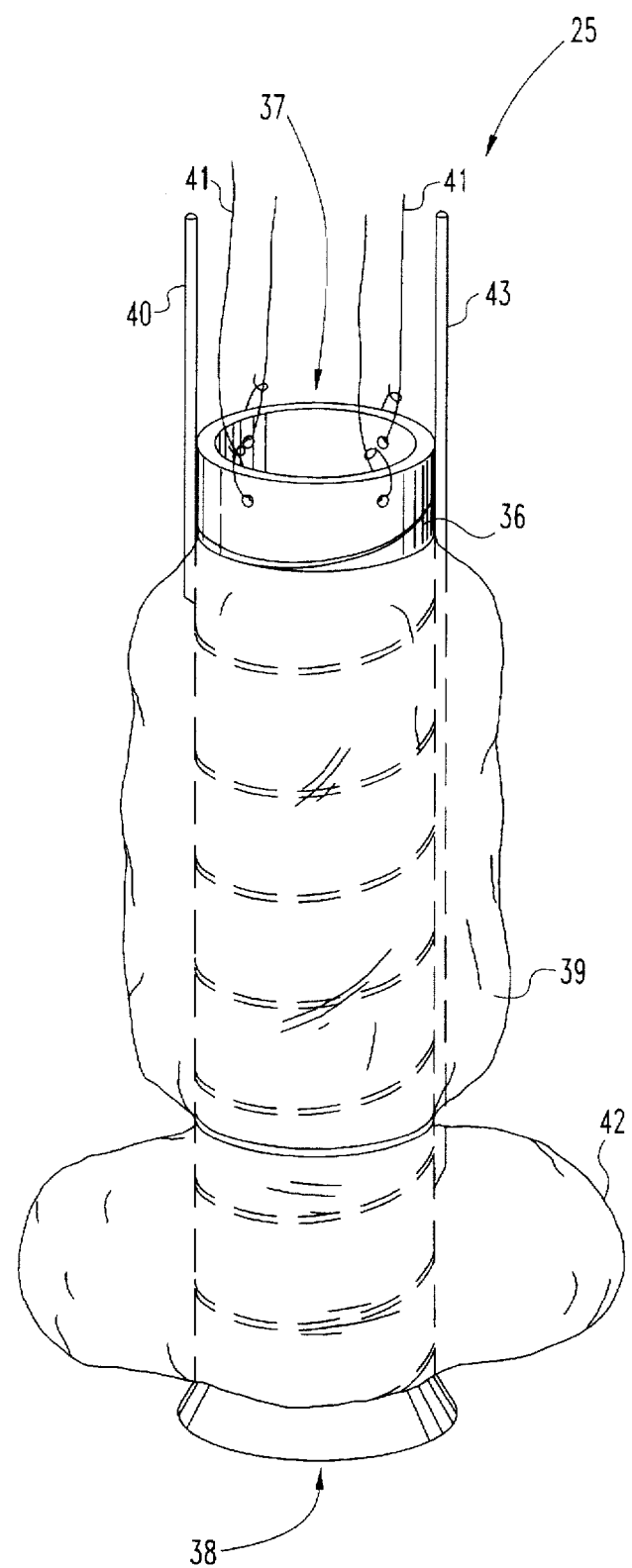
FIG. 2 is a perspective view of the balloon tamponade device comprising a portion of FIG. 1.

Referring to FIG. 2, there is illustrated a perspective view of the preferred embodiment of balloon tamponade device 25. However, it is contemplated that there are other expandable tamponade devices that can pass over and along the irrigation tube 11 and assist in controlling internal bleeding. The Applicant incorporates herein by reference U.S. Pat. No. 5,308,326 describing a Balloon Tamponade Device and Methods for Their Placement. The balloon tamponade device 25 includes a tube 36, a proximal open end 37 and a distal open end 38. An inflatable esophageal balloon 39 is mounted over the tube 36 and an inflation tube 40 is provided for directing pressurized fluid to inflate the esophageal balloon 39.

Wires 41 are attached to the tube 36 and generally form a bridal for securing the balloon tamponade device 25 to a traction instrument (not illustrated). In one form of the present invention the wires 41 extend up the esoph agus 13 thereby allowing the device 25 to be secured in place while the proximal open end 37 of the tube 36 is positioned within the esophagus 13. A gastric balloon 42 is mounted over the tube 36 and is adapted to seat against the gastric cardia 70 when inflated in the stomach 14 and thereafter the balloon tamponade device 25 is drawn upward by the wires 41. A s econd separate inflation lumen 43 is provided to inflate the gastric balloon 42. The inflation lumens 40 and 43 being connectable to an external fluid pressurizing sources (not illustrated). Further, details regarding the preferred balloon tamponade device are disclosed in U.S. Pat. No. 5,308,326 which has been incorporated herein by reference. It is understood that other balloon tamponades can be ut ilized with the present invention.

Figure 3:
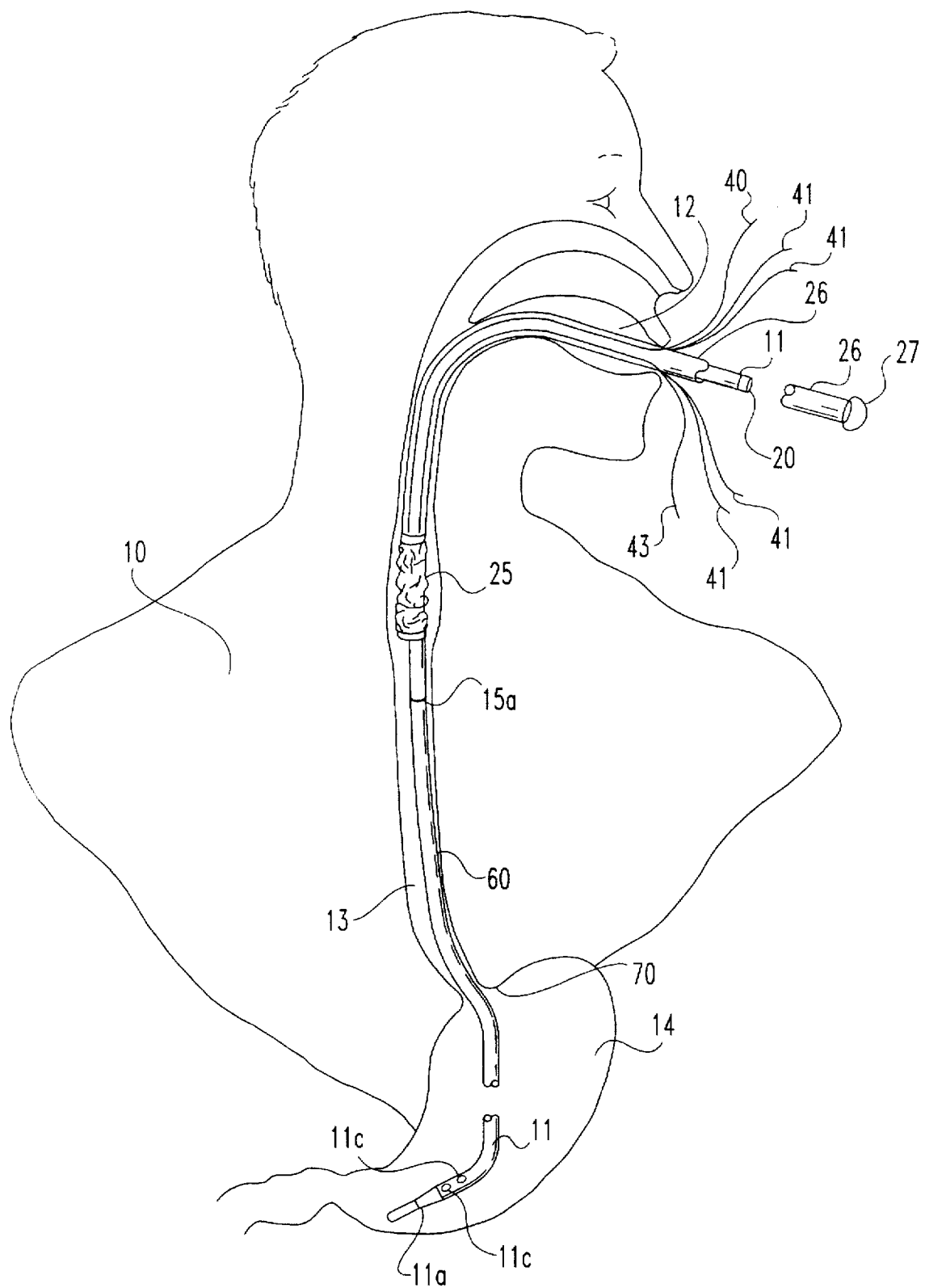
FIG. 3 is a perspective view of FIG. 1 having the balloon tamponade device advanced along the irrigation tube within the patient.
Figure 4:
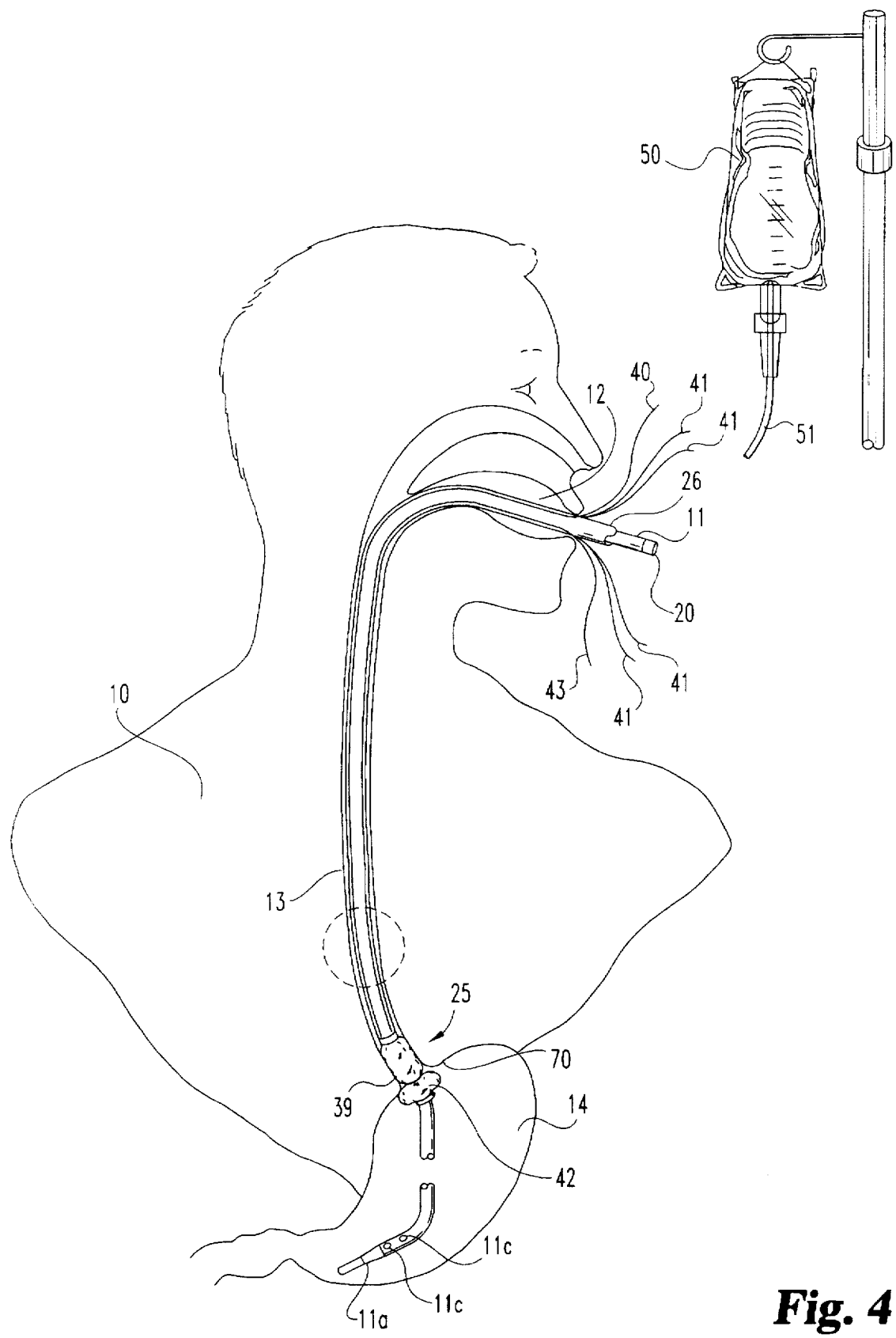
FIG. 4 is a perspective view of FIG. 1 having the balloon tamponade device inflated and positioned adjacent the distal end of the esophagus.
Figure 5:
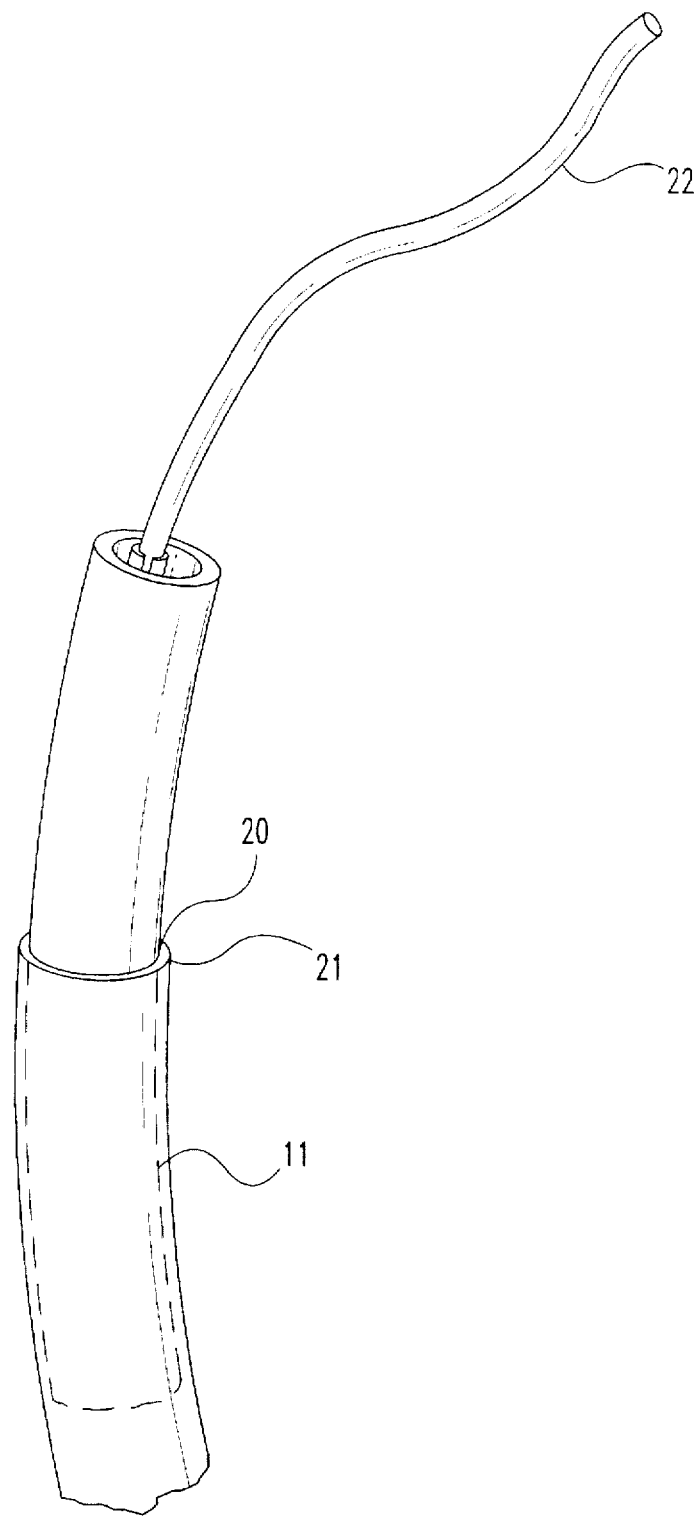
FIG. 5 is a enlarged view of the FIG. 4 irrigation tube with an obturator and wire guide therein.

Referring to FIGS. 3 and 4, there is illustrated the balloon tamponade device 25 being positioned along the irrigation tube 11 within the esophagastric system of the patient. It is preferred that the balloon tamponade device 25 be deployed in an uninflated state by placing the balloon tamponade device 25 onto the irrigation tube 11 extending from the patients mouth 12 and then utilizing the pushing member 26 to apply a force sufficient to move the device 25 through the esophagus 13 and into the stomach 14. Pushing member 26 is designed to fit around the outer circumferential surface of the irrigation tube 11 and adjacent the balloon tamponade device 25. The party wishing to deploy the balloon tamponade device 25 must exert a force sufficient to overcome any resistance associated with the esophagus 13 structure. Having pushed the balloon tamponade 25 along the outer surface of the irrigation tube 11 it will arrive in the proximal portion of the stomach as illustrated in FIG. 4.

Upon inflating and positioning the ga stric balloon 42 and esophageal balloon 39 they function to apply a compressive force to distal end of the esophagus 13 and the proximal end of the s tomach 14 in order to control bleeding from the esophagogastric varices. In the preferred embodiment, the irrigation tube 11 extends 20 centimeters (7.9 inches) within the patient's stomach after th e balloon tamponade device has been positioned adjacent the gastric cardia 70. An external fluid source 50 for use in irrigating the stomach 14 is connectable with the irrigation tube 11 to a llow the practitioner to irrigate the stomach. Further, a syringe or other aspiration device is connectable to the distal end 11b of irrigation tube 11 in order to aspirate the contents of the stomach. The passage of the irrigation tube 11 allows for the practitioner if necessary to obtain a sample and/or irrigate and aspirate the stomach prior to, during and subsequent to the deployment of the balloon tamponade device 25. With reference to FIG. 1a there is illustrated a fluid connection adapter 30 that can be utilized to connect the irrigation tube 11 to a tube 51 extending from the fluid source 50.

With reference to FIGS. 1–5 there will be illustrated a method of deploying the balloon tamponade device 25 over irrigation tube 11. Irrigation tube 11 and pushing member 26 can be utilized by a physician, a nurse, an emergency technician, and even a trained individual for the deployment of the balloon tamponade device 25. The flexibility in types of people who can deploy the balloon tamponade device without an endoscope allows for use in places remote from physicians offices and medical emergency rooms. Thus the potentially lifesaving technique of using a balloon tamponade device to prevent bleeding can be utilized in situations that heretofore were not available.

The practitioner/party wishing to introduce the balloon tamponade device 25 begins by passing the irrigation tube 11 into the patient's mouth 12, down the esophagus 13, and into the stomach 14. The length of tube 11 deployed is controllable by the party and generally the tube 11 is placed such that about 60 centimeters (23.6 inches) extend from the patient's mouth 12. The sizing of the tube 11 facilitates placement of the irrigation tube 11 by a non physician and prepositions the appropriate length of tubing within the stomach 14. An internal obturator 20 is positioned within the irrigation tube 11 during passage within the patient in order to minimize or eliminate kinking of the tube 11. The balloon tamponade 25 is then placed over the external surface of irrigation tube 11 extending adjacent the patient's mouth 12 and then advanced along the tube 11 into position in the patient's stomach 14. Pushing member 26 is slidable over the external surface of tube 11 and adjacent device 25 in order to deliver the necessary force to move the balloon tamponade device 25 to the desired location. It is understood that pushing member 26 advances along the irrigation tube 11.

The practitioner/party upon having placed the balloon tamponade device 25 in the proximal end of the stomach, inflates balloon 42, pulls upward on the bridle, and then inflates balloon 39. The inflated balloons 39 and 42 respectively provide sufficient compressive force to treat the bleeding esophageal varices. The guide wires 41 are pulled by the practitioner/party to control movement of the balloon tamponade device 25 within the esophagogastric tract, if necessary. Obturator 20 is removable from tube 11 and upon its removal aperture 21 is available for the passage of fluid therethrough to irrigate and aspirate the stomach. It is understood that obturator 20 is also removable prior to the passage of the balloon tamponade device into the patient thereby allowing the practitioner to obtain a sample of the gastric contents or irrigate and aspirate within the patient's stomach before treatment by balloon tamponade. Further, the practitioner can obtain samples at any other time from the patients stomach during the medical procedures.

While the inventaion has been illustrated and described in detail in the drawings and foregoing description, the same is to be consideed as illustrative and not restrictive in character, it being understood that only the preferred embodiment has been shown and described and that all changes and modifications that come within the spirit of the invention are desired to be protected.

What is claimed:

1. An apparatus for controlling esophagastric bleeding within a patient, comprising:

an elongated flexible member, a portion of said elongated member passable in the oral-gastric tract of the patient;

a tamponade device disposed on and slidable along an outer surface of said elongated flexible member; and a pushing member disposed adjacent said tamponade for moving said tamponade along said flexible member, wherein the pushing member is a tube having a passageway extending therethtough and is slidably disposed about at least a portion of said elongated flexible member.

2. The apparatus of claim 1 wherein:

said elongated flexible member has a distal end opposite said portion, and said tamponade device is slidable over said distal end.

3. The apparatus of claim 1 wherein:

said elongated flexible member having a passageway extending therethrough, and further including an obturator extending within said passageway for minimizing the kinking of said tube during the passage of said portion within the patient.

4. The apparatus of claim 3 wherein:
said tube is about 120 cm in length.

5. The apparatus of claim 1 wherein:
said elongated flexible member is about 10.7 mm in diameter.

6. A combination, comprising:

a flexible tube having a proximal portion passable through a patient's mouth and into the stomach, and a distal portion opposite said proximal portion;

a balloon tamponade for controlling bleeding within the patient's esophagastric system, said tamponade disposed on and slidable over said distal portion end and along an outer surface of said tube, further said tube having an internal passageway extending therethrough;

a pushing member disposed adjacent said tamponade for moving said tamponade along said flexible tube; and an obturator extending within said passageway for preventing kinking of said tube during the passage of said tube within the patient.

7. An apparatus for controlling esophagastric bleeding within a patient, comprising:

an elongated flexible member positionable within the patient to form a passageway between the mouth and stomach, said member having an aperture therethrough for the passage of fluid;

a tamponade disposed on and slidable along said elongated flexible member; said tamponade for controlling bleeding; and a pushing member positionable adjacent said tamponade for advancing said tamponade along said flexible member, wherein the pushing member is a tube having a passageway extending therethrough and is slidably disposed about at least a portion of said elongated flexible member.

8. The apparatus of claim 7 wherein:
said elongated flexible member includes a proximal end positionable within the stomach and a distal end; and
said tamponade disposed on said distal end and slidable along said elongated flexible member toward said proximal end.

9. The apparatus of claim 7, wherein:
said elongated tubular member includes a proximal end positionable within the stomach; and
said proximal end includes a plurality of apertures for fluid exchange with the patient's stomach.

10. An apparatus for controlling esophagastric bleeding within a patient, comprising:

a flexible tube having a proximal portion passable through a patient's mouth and into the stomach, and a distal portion opposite said proximal portion, said tube having an internal passageway extending therethrough;

a balloon tamponade for controlling bleeding within the patient's esophagastric system, said tamponade slidable over said distal portion and along an outer surface of said tube toward said proximal portion;

a pushing member disposed adjacent said tamponade for moving said tamponade along said flexible member, wherein the pushing member is a tube having a passageway extending therethrough and is slidably disposed about at least a portion of said elongated flexible member; and an obturator extending within said passageway for substantially preventing kinking of said tube during the passage of said tube within the patient.

11. A method for deploying a balloon tamponade for controlling esophagastric bleeding through a patient's mouth and into their stomach, comprising:

providing a flexible tube having a proximal end and a distal end;

passing at least a portion of the tube through the patient's mouth and into the stomach, the proximal end of the tube being positionable within the stomach and the distal end of the tube adjacent the mouth;

positioning the balloon tamponade around the distal end of the tube adjacent the mouth; and advancing the balloon tamponade along the tube towards the proximal end thereof.

12. The method of claim 11 wherein:
said providing includes an obturator disposed within said flexible tube; and further including removing the obturator after said passing.

13. The method of claim 11 wherein:
said advancing includes positioning a pusher member into abutting engagement with the balloon tamponade and moving the pusher member;*owards the proximal end of the tube, thereby moving the balloon tamponade along the flexible tube towards the proximal end thereof.

14. The method of claim 13 which further includes removing the pusher member after the balloon tamponade is positioned near the proximal end of the flexible tube.

\* \* \* \* \*

UNITED STATES PATENT AND TRADEMARK OFFICE
CERTIFICATE OF CORRECTION

PATENT NO : 5,785,684
DATED : July 28, 1998
INVENTOR(S) : David S. Zimmon

It is certified that error appears in the above-identified patent and that said Letters Patent is hereby corrected as shown below:

In column 6, line 40, please change "consideed" to --considered--.
In column 6, line 55, please change "threthtough" to --therethrough--.
In column 8, line 42, please change "*owards" to --towards--.

Signed and Sealed this

Thirty-first Day of August, 1999

Attest:

Q. TODD DICKINSON

Attesting Officer

Acting Commissioner of Patents and Trademarks